US011701241B2

United States Patent
McLean (10) Patent No.: US 11,701,241 B2
(45) Date of Patent: Jul. 18, 2023

(54) BELLOWS SHAPED SPINAL IMPLANT

(71) Applicant: SPINE WAVE, INC., Shelton, CT (US)

(72) Inventor: Scott McLean, Sandy Hook, CT (US)

(73) Assignee: SPINE WAVE, INC., Shelton, CT (US)

( * ) Notice: Subject to any disclaimer, the term of this patent is extended or adjusted under 35 U.S.C. 154(b) by 0 days.

(21) Appl. No.: 17/847,873

(22) Filed: Jun. 23, 2022

(65) Prior Publication Data

US 2022/0409390 A1 Dec. 29, 2022

Related U.S. Application Data

(60) Provisional application No. 63/215,593, filed on Jun. 28, 2021.

(51) Int. Cl.
*A61F 2/44* (2006.01)
*A61F 2/46* (2006.01)
*A61F 2/30* (2006.01)

(52) U.S. Cl.
CPC ...... *A61F 2/447* (2013.01); *A61F 2002/3092* (2013.01); *A61F 2002/3093* (2013.01); *A61F 2310/00023* (2013.01)

(58) Field of Classification Search
CPC .... A61F 2/44; A61F 2/447; A61F 2002/3092; A61F 2002/3093; A61F 2002/00023; A61F 2002/30907; A61F 2002/30909; A61F 2002/30915; A61F 2002/30919
USPC ............................................ 623/17.11–17.16
See application file for complete search history.

(56) References Cited

U.S. PATENT DOCUMENTS

| 4,932,969 A | * | 6/1990 | Frey ........................ A61F 2/441 623/17.12 |
| 5,002,576 A | * | 3/1991 | Fuhrmann ............... A61F 2/441 606/247 |
| 5,674,294 A | * | 10/1997 | Bainville ................ A61F 2/442 623/17.16 |

(Continued)

FOREIGN PATENT DOCUMENTS

DE 90 00 094 U1 1/1991

OTHER PUBLICATIONS

Drake Medical Plastics, "What Benefits Do PEEK Spinal Cages Offer Patients?", 5 pages, Copyright 2021.

(Continued)

*Primary Examiner* — Jessica Weiss
(74) *Attorney, Agent, or Firm* — Hoffmann & Baron, LLP (57) ABSTRACT

A bellows shaped spinal implant, comprising an upper plate having an upper opening therethrough, a lower plate having a lower opening therethrough, and aa bellows shaped shell extending between and joining the upper plate and the lower plate. The bellows shaped shell is formed of titanium or an alloy comprising titanium and includes a wall extending continuously therearound that defines a hollow interior in communication with the upper opening and the lower opening. The wall has a thickness in the range of 0.5 mm to 1.0 mm to provide for radiographic imaging through the wall. The wall is angled or curved inwardly or outwardly between the upper plate and the lower plate to provide stiffness that mimics the stiffness properties of a similarly sized polyetheretherketone (PEEK) implant.

29 Claims, 13 Drawing Sheets

(56) References Cited

U.S. PATENT DOCUMENTS

| | | | |
|---|---|---|---|
| 6,264,695 B1* | 7/2001 | Stoy | A61L 27/44 |
| | | | 623/17.16 |
| 6,395,032 B1 | 5/2002 | Gauchet | |
| 6,527,804 B1 | 3/2003 | Gauchet et al. | |
| 6,579,320 B1* | 6/2003 | Gauchet | A61F 2/442 |
| | | | 623/17.15 |
| 6,582,468 B1 | 6/2003 | Gauchet | |
| 6,981,989 B1 | 1/2006 | Fleischmann et al. | |
| 7,166,131 B2 | 1/2007 | Studer et al. | |
| 7,578,848 B2 | 8/2009 | Mbert et al. | |
| 7,585,324 B2 | 9/2009 | Mbert et al. | |
| 7,892,285 B2 | 2/2011 | Viker | |
| 7,918,888 B2 | 4/2011 | Hamada | |
| 11,185,423 B2 | 11/2021 | Tipping | |
| 11,446,159 B2 | 9/2022 | Mirda et al. | |
| 2002/0128716 A1* | 9/2002 | Cohen | A61F 2/4465 |
| | | | 623/17.13 |
| 2004/0024407 A1 | 2/2004 | Ralph et al. | |
| 2005/0228500 A1* | 10/2005 | Kim | A61F 2/442 |
| | | | 623/17.13 |
| 2006/0149381 A1 | 7/2006 | Kim | |
| 2006/0241765 A1 | 10/2006 | Burn et al. | |
| 2009/0069895 A1* | 3/2009 | Gittings | A61F 2/442 |
| | | | 623/17.11 |
| 2009/0069896 A1* | 3/2009 | Reo | A61F 2/442 |
| | | | 623/17.11 |
| 2011/0082552 A1* | 4/2011 | Wistrom | A61F 2/4425 |
| | | | 623/17.16 |
| 2011/0238185 A1 | 9/2011 | Filippi et al. | |
| 2012/0089227 A1* | 4/2012 | Jarzem | A61F 2/44 |
| | | | 623/17.12 |
| 2012/0316650 A1* | 12/2012 | Ullrich, Jr. | A61F 2/4455 |
| | | | 29/592 |
| 2019/0008651 A1 | 1/2019 | Doty | |
| 2020/0138594 A1 | 5/2020 | Renganath et al. | |
| 2020/0197565 A1 | 6/2020 | Suh et al. | |
| 2022/0233330 A1 | 7/2022 | Gray et al. | |
| 2022/0296386 A1 | 9/2022 | Fang et al. | |

OTHER PUBLICATIONS

International Search Report in PCT Application No. PCT/US2022/034709, dated Oct. 19, 2022, 3 pages.

Written Opinion in PCT Application No. PCT/US2022/034709, dated Oct. 19, 2022, 3 pages.

* cited by examiner

BELLOWS SHAPED SPINAL IMPLANT

CROSS-REFERENCE TO RELATED APPLICATION

This application claims the benefit of U.S. Provisional Patent Application No. 63/215,593, filed Jun. 28, 2021, the entire contents of which are incorporated by reference herein.

FIELD OF THE INVENTION

The subject invention relates generally to the field of spinal implants and more particularly to a spinal interbody fusion device that is configured to mimic the biomechanical properties of the spine and provide radiolucency for radiographic observation of the fusion process.

BACKGROUND OF THE INVENTION

Spinal implants such as interbody fusion devices are used to treat degenerative disc disease and other damages or defects in the spinal disc between adjacent vertebrae. The disc may be herniated or suffering from a variety of degenerative conditions, such that the anatomical function of the spinal disc is disrupted. Most prevalent surgical treatment for these conditions is to fuse the two vertebrae surrounding the affected disc. In most cases, the entire disc will be removed, except for a portion of the annulus, by way of a discectomy procedure. A spinal interbody fusion device is then introduced into the intradiscal space and suitable bone graft, or bone substitute material is placed substantially in and/or adjacent the device in order to promote fusion between two adjacent vertebrae.

Spinal interbody fusion devices, some of which are expandable and others of fixed dimension, may be used to treat spinal conditions in the cervical, thoracic and lumbar regions of the spine. In cervical fusion, such devices are introduced anteriorly while in thoraco-lumbar surgery, the device may also be inserted in a posterior, lateral or transforaminal approach. The particular approach selected is primarily determined by the type of treatment to be administered by the surgeon. In order to accommodate the spinal anatomy and promote arthrodesis, an interbody fusion device preferably mimics the biomechanical properties of the spine and optimizes contact to achieve osteointegration with adjacent endplates of opposing vertebral bodies.

In addition to the size and configuration of a spinal interbody fusion device, the materials used in the device are a significant factor for a successful spinal fusion procedure. While the material for a spinal interbody fusion device must be biocompatible, other properties to be considered include strength, stiffness, fatigue and radiolucency. For many years titanium has been a material of choice not only for its biocompatibility with the human body, but also because it is sturdy and strong and fuses readily with bone. While providing desirable osteointegration with bone, titanium has issues in providing required flexibility and resilience in the disc space. Further, as titanium lacks sufficient radiolucency it often obscures attempts to image the surgical site. Synthetic materials have been developed over the recent years as an alternative to titanium, such as polyetheretherketone (PEEK). PEEK has physical properties that are similar to bone and is inherently translucent allowing imaging transparency. Unfortunately, PEEK does not provide osteointegration with bone. As a result, and in an effort to enhance fusion with bone, spinal implants formed of PEEK are sometimes coated with a titanium layer on the surfaces that interface with adjacent vertebral body endplates.

Accordingly, there is a still a desire to develop an interbody fusion device that beneficially combines the sturdiness, strength and osteointegration characteristics of titanium with the radiolucency and biomechanical properties of PEEK that are similar to bone.

SUMMARY OF THE INVENTION

It is an object of the invention to provide a bellows shaped spinal implant comprising a bellows shaped shell having a wall that is configured and dimensioned to achieve radiographic imaging therethrough, the wall being inwardly angled and dimensioned to provide stiffness that mimics the stiffness properties of a similarly sized polyetheretherketone (PEEK) implant.

It is another object of the invention to provide a bellows shaped spinal implant comprising outer upper and lower contact surfaces for contacting endplates of opposing vertebral bodies, the contact surfaces being formed to have a micro roughness, at least a portion of each contact surface being altered to include a nano roughness.

DESCRIPTION OF THE EMBODIMENTS

For the purposes of promoting and understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 1:
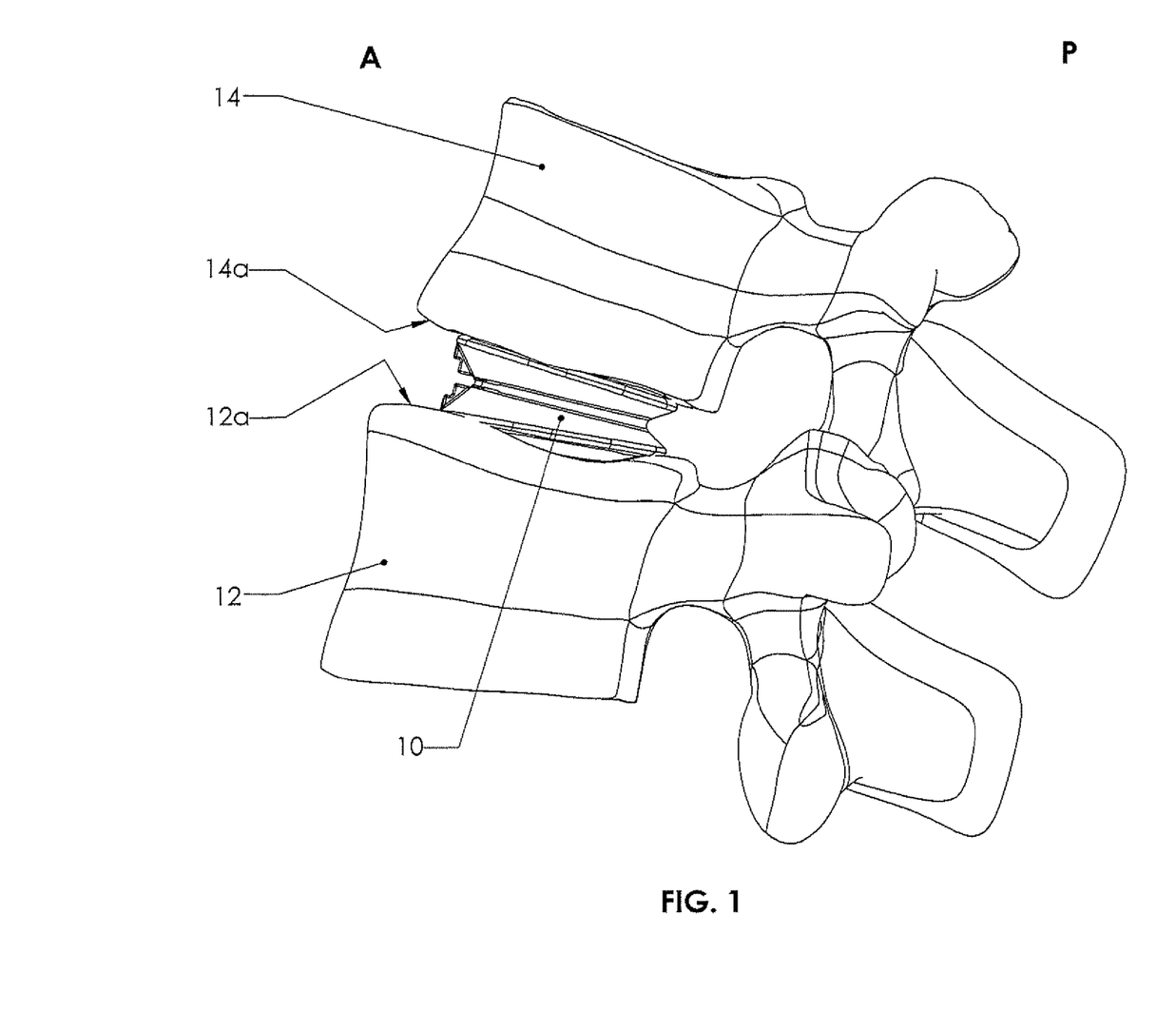
FIG. 1 is a lateral elevation view of a lumbar portion of a human spine with a bellows shaped spinal implant according to an embodiment of the present invention configured as an anterior lumbar interbody fusion device (ALIF) having been placed in position between two opposing vertebral bodies.
Figure 2:
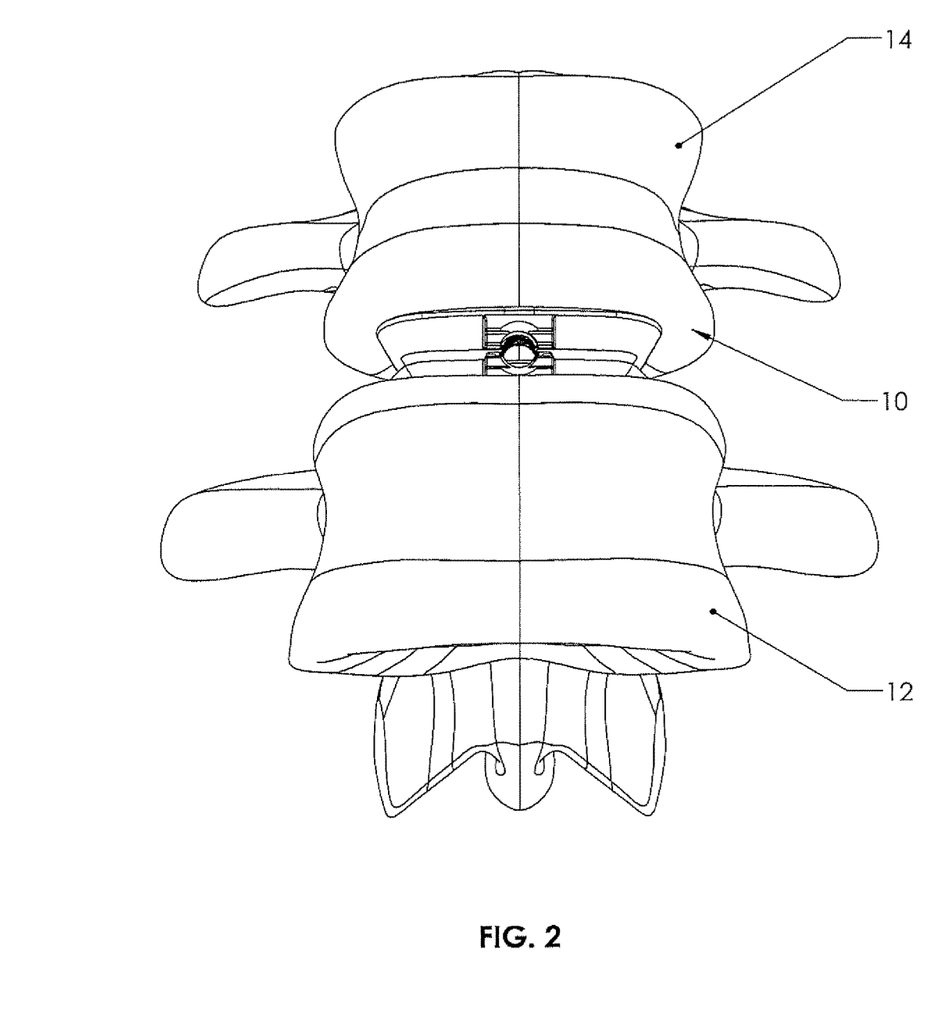
FIG. 2 is a view of FIG. 1 as seen from the anterior direction.

Referring to FIGS. 1 and 2, there is shown a segment of the lumbar region of a human spine into which a bellows shaped spinal implant 10 in accordance with a particular arrangement of the invention has been inserted. In this particular arrangement, spinal implant 10 is sized and configured as an anterior lumbar interbody fusion (ALIF) device that is introduced between opposing vertebral bodies 12 and 14 from an anterior (A) direction toward the posterior (P) portion of the spine. As shown, bellows shaped spinal implant 10 is a conventional ALIF device in that supplemental fixation in the form of plates and/or rods are used in conjunction with the spinal implant 10 to secure spinal implant 10 in place subsequent to insertion. As will be described, a bellows shaped spinal implant configured as a standalone version is also contemplated. It should be appreciated that bellows shaped spinal implant 10 may also be configured for insertion into other portions of the spine, such as the thoracic region and the cervical region.

Figure 3:
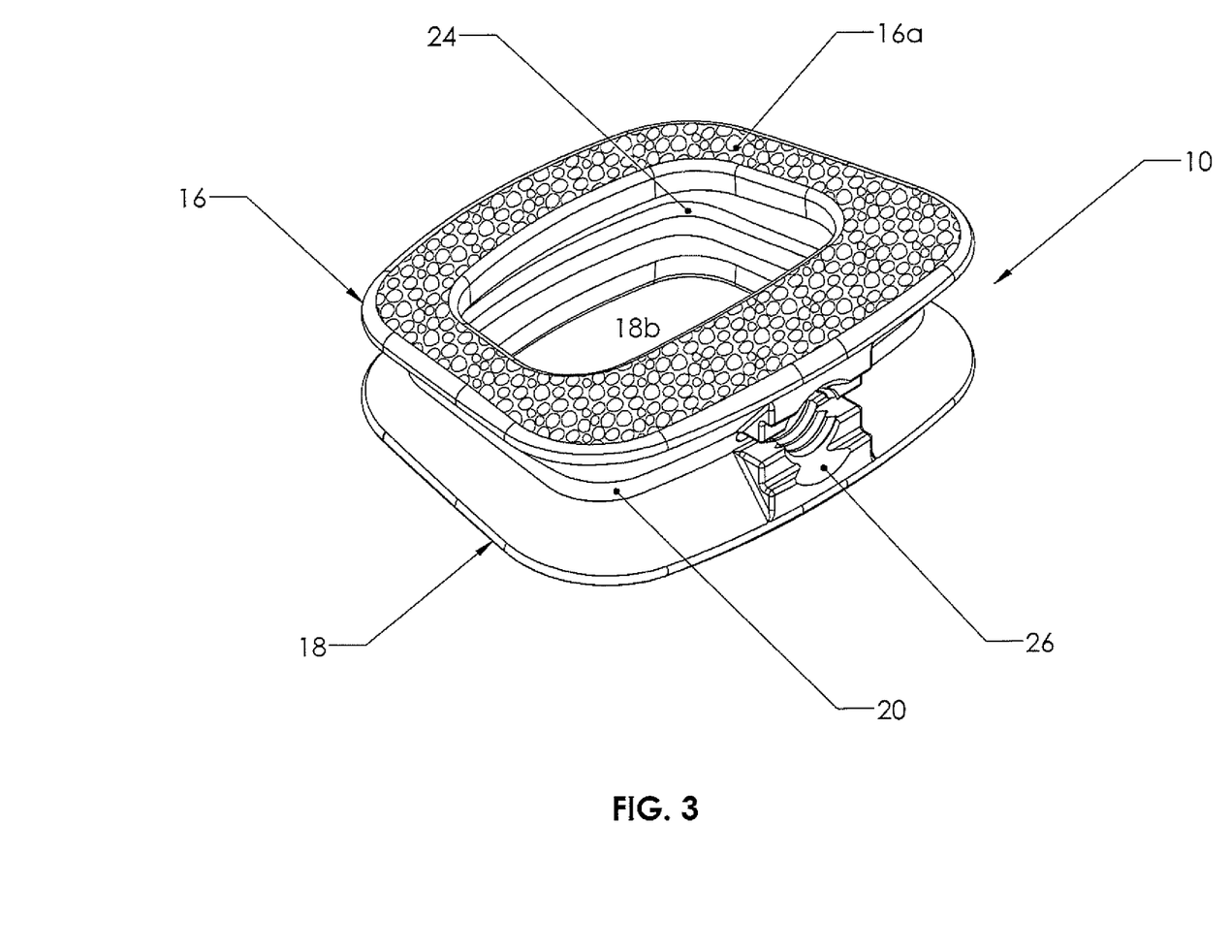
FIG. 3 is a top perspective view of the bellows shaped ALIF as seen from the anterior direction.
Figure 4:
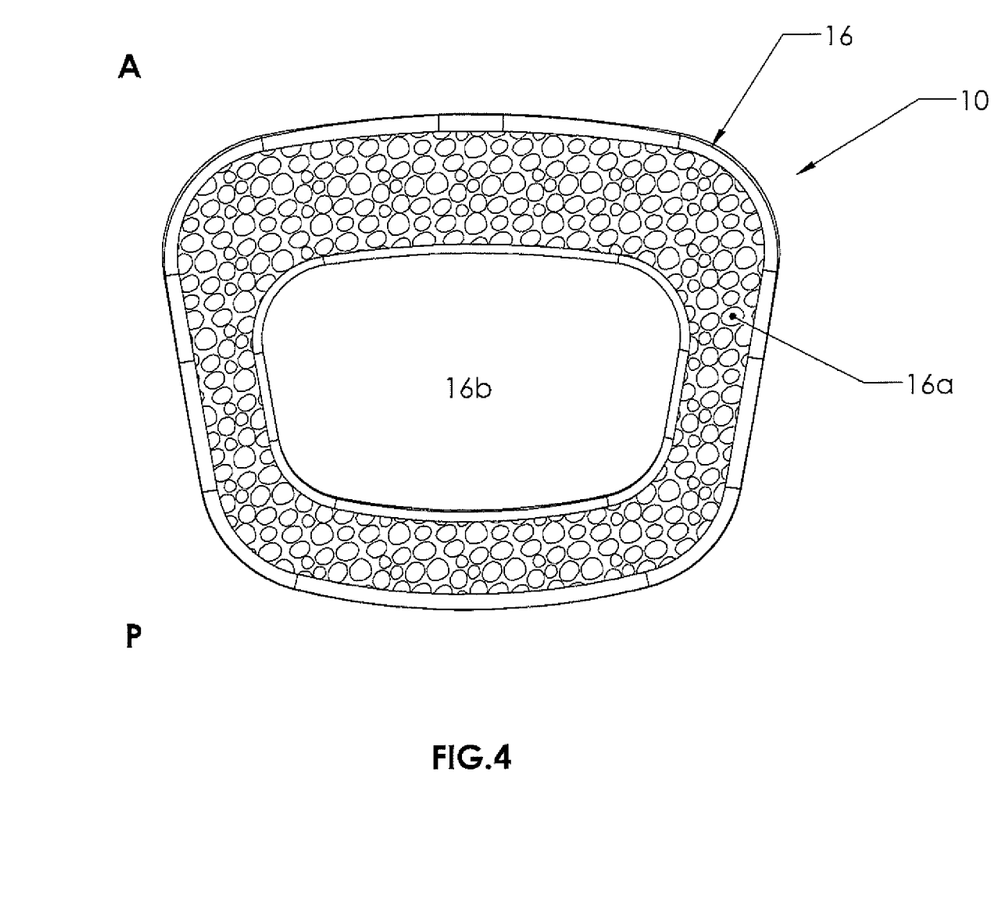
FIG. 4 is a top plan view of the bellows shaped ALIF device of FIG. 3.
Figure 5:
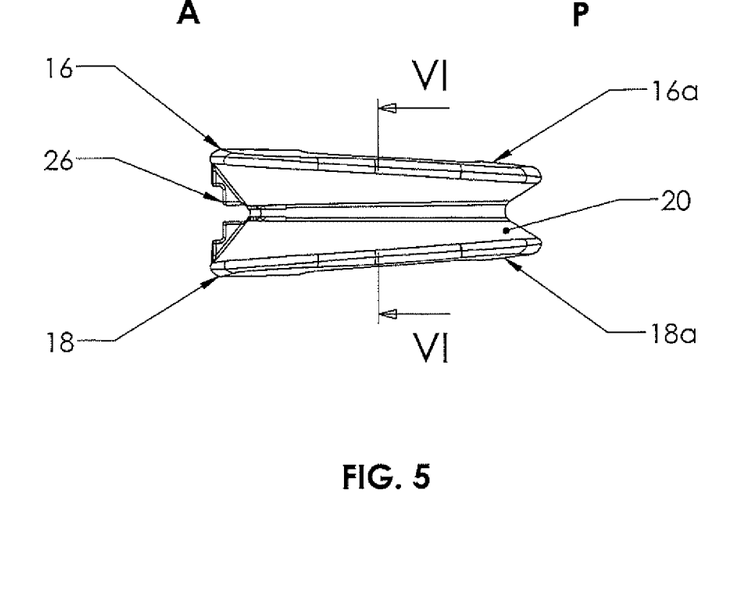
FIG. 5 is a lateral elevation view of the bellows shaped ALIF device of FIG. 3.
Figure 6:
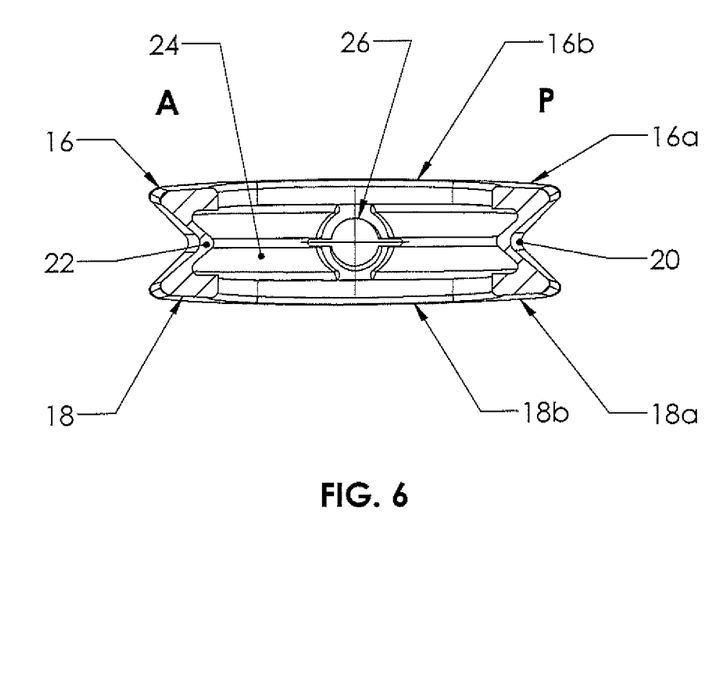
FIG. 6 is a cross-sectional view of the bellows shaped ALIF device as seen along viewing lines VI-VI of FIG. 5.

Turning now to FIGS. 3-8, details of the bellows shaped spinal implant 10 are described. Spinal implant 10 comprises an upper plate 16 and a lower plate 18 that are joined together by a bellows shaped shell 20. Upper plate 16 has a contact surface 16a configured to contact the endplate 14a of superior vertebral body 14 and lower plate 18 is a contact surface 18a configured to contact the endplate 12a of inferior vertebral body 12. Contact surfaces 16a and 18a may be generally planar and angled downwardly from the anterior (A) to the posterior (P) direction as illustrated in FIG. 5 so as to provide suitable lordosis upon insertion between vertebral bodies 12 and 14. Such a downward angle may be, for example, between 0 and 30 degrees. Contact surfaces 16a and 18a may be slightly curved along the lateral direction as illustrated in FIG. 6 so as to provide a more suitable anatomic contact with vertebral body endplates 14 and 16, respectively. As shown in FIGS. 3 and 4, lower plate 18 has a central opening 18b and upper plate 16 has a central opening 16b.

Figure 7:
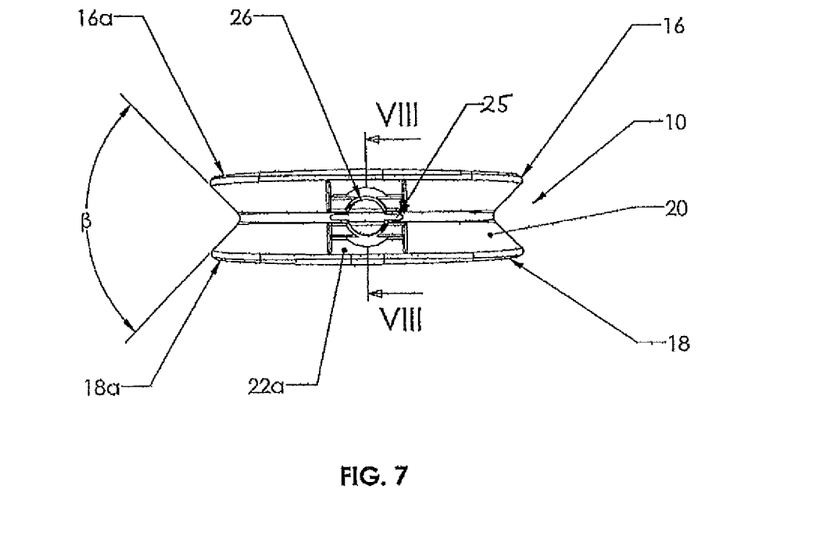
FIG. 7 is an anterior elevation view of the bellows shaped ALIF device of FIG. 3, the shell wall of the ALIF device being inwardly angled or curved.
Figure 8:
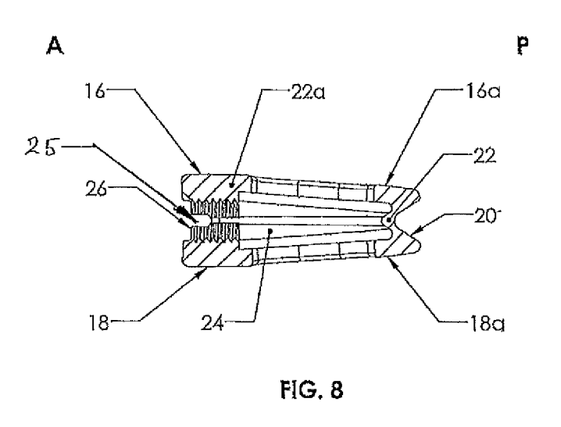
FIG. 8 is a cross-sectional view of the bellows shaped ALIF device as seen along viewing lines VIII-VIII of FIG. 7.

Shell 20, as seen more particularly in FIGS. 5-8, is configured to have a bellows shape having a relatively thin wall 22 extending around the periphery of shell 20, wall 22 defining a hollow interior 24. Hollow interior 24 provides a space for bone graft material and is in fluid communication with central opening 16b of upper plate 16 and with central opening 18b of lower plate 18. Wall 22 is angled or curved inwardly between upper plate 16 and lower plate 18 and flares outwardly in both directions toward upper plate 16 and lower plate 18, respectively. As such as shown in FIG. 7, an angle beta, β is formed in wall 22. Wall 22 may be provided with a relatively thicker portion 22a at the anterior (A) end as shown in FIGS. 7 and 8 through which a threaded hole 26 may be formed for insertion and graft delivery purposes, as will be described. In some instances, a suitable slit 25 or cut may be provided laterally into thicker portion 22a so as to minimize stiffening of implant 10. It should also be understood that wall 22 of bellows shaped shell 20, although not shown, may be angled or curved outwardly from each of upper plate 16 and lower plate 18 toward a location between upper plate 16 and lower plate 18.

In the particular arrangement being described, upper plate 16, lower plate 18 and bellows shaped shell 20 are formed unitarily as a one-piece bellows shaped spinal implant 10. More particularly in this arrangement, bellows shaped spinal implant 10 is formed of titanium. As noted hereinabove, titanium has desirable implant properties including biocompatibility, strength and osteointegration capability. While lack of radiolucency and relatively high stiffness may be considered drawbacks when considered against polymers such as polyetheretherketone (PEEK), such deficiencies are offset by the hollow bellows configuration of spinal implant 10. It has been found, for example, that when wall 22 of bellows shaped shell 20 is formed to have a thickness of approximately 0.5 mm radiographic imaging is achievable through wall 22 into hollow interior 24. Such imaging would tend to degrade with increased thickness, likely resulting in a loss of the radiographic benefit with a wall thickness greater than about approximately 1.0 mm. In addition, a wall thickness of less than approximately 0.5 mm may detrimentally weaken spinal implant 10 as well as potentially impacting manufacturability.

In addition to the benefit of radiolucency, the hollow bellows configuration of spinal implant 10 provides a beneficial impact on desired stiffness. It has been found that the thin walled hollow bellows shell 20 allows a degree of flexibility to spinal implant 10 by inducing bending stresses when the implant 10 is under compression. Such induced bending tends to reduce stiffness. The stresses in wall 22 as a result of such bending vary as a function of the angle beta, β for an inwardly curved wall 22. The more acute the angle beta, β, the more bending stresses occur and less direct compression occurs through wall 22. In turn, higher levels of deflection occur in configurations when the angle beta, β is more acute, tending to weaken the structure and making it less stiff. It is known that low stiffness promotes load sharing in accordance with Wolfs law with bone graft material contained in hollow interior 24. From a stiffness standpoint, the angle beta, β of inwardly curved wall of shell 20 may range from a minimum of approximately 0° to a maximum of approximately 180°. However, in some instances and sizes of spinal implant 10 having an inwardly curved wall 22, overly acute angles may be less desirable as excessive inward projection of the walls 22 would result in loss of internal volume for bone graft and may tend to decrease the stability of implant 10. Similarly, angles above 180° may be used to provide a similar effect regarding stiffness characteristics with an outwardly curved wall 22. However, angles above 180° may be less desirable due to the increased overall dimensions of the implant compared to the dimension of the contact surface, thereby requiring a larger entry corridor for implantation. It should be appreciated that a similar effect could be achieved without increasing the implant dimensions using angles above 180° if the wall 22 joins upper plate 16 and lower plate 18 at a location inset from the edges of upper plate 16 and lower plate 18. It should now be appreciated that walls 22 having appropriate inward or outward curvature may be utilized to effectively control implant stiffness.

It is noted that the angle beta, β may vary as a function of implant height to maintain desired stiffness characteristics. Shorter height implants would typically require more acute angles than taller heights due to the relationship between height and stiffness. Taller implants would typically be relatively less stiff so less acute angles would be needed to reduce stiffness A spinal implant 10 having an angle beta β, for example, of approximately 180° would result from a shell wall 22 being relatively straight. Such an implant may be made to have a height and wall thickness that would provide sufficient resiliency to reduce implant stiffness and may be used in spinal procedures, such as cervical corpectomies.

Further to the beneficial impact on radiolucency and low stiffness, the formation of bellows shaped spinal implant 10 from titanium allows for the promotion of rapid fixation of spinal implant 10 to endplates 12a and 14a of vertebral bodies 12 and 14. For example, contact surfaces 16a and 18a of upper plate 16 and lower plate 18, respectively, may be readily altered to enhance bone apposition by a 3-D printing process that would provide a porous surface with micro roughness. Such pores would be in communication with hollow interior 24 for through growth fusion of bone graft to vertebral endplates 12a and 14a. Additionally, the micro roughness of contact surfaces 16a and 18a may then be further augmented to add a nano roughness surface by laser ablation using, for example, a femto-second laser process. Alternatively, an acid etching process could be used to alter the roughness of contact surfaces 16a and 18a to include micro and nano roughness. Furthermore, the contact surfaces 16a and 18a may be modified to alter the micro and nano-roughness by a combination nano-second and femto-second laser process, or by the femto-second laser process alone by varying selected parameters, such as the pulse duration or frequency of the laser process, or the quantity of energy applied. Accordingly, the desired surface roughness may be achieved by various methods, including without limitation, laser ablation, acid etching or a combination of both.

In one example of bellows shaped spinal implant 10 that is particularly configured for use as an ALIF device, the anterior height as depicted in FIG. 5 may range from 8 to 20 mm and the posterior height may range from 4 to 16 mm. As observed from FIG. 4, the anterior/posterior depth may range from 22 to 30 mm and the medial/lateral width may range from 24 to 42 mm. The thickness of each of the upper plate 16 and the lower plate 18 may be about 2 mm. The thickness of shell wall 22 may be approximately 0.5 mm and the angle beta, β of bellows shaped shell 20 may be approximately 90°. A plurality of spinal implants 10 having different sizes and dimensions may be provided in a kit to allow the spinal surgeon to select the appropriate spinal implant 10 based upon the surgical needs and the anatomy of the patient. Prior to such selection, one or more trial devices simulating the size and configuration of a spinal implant 10 needed for a particular surgery may be provided. Once a proper spinal implant 10 is determined and chosen, it may be inserted into the lumbar spine between vertebral bodies 12 and 14 by attaching a portion of a suitable threaded inserter into threaded hole 26 of spinal implant 10. Spinal implant 10 is then manually urged by such inserter from an anterior direction between endplates 12a and 14a to the position shown in FIGS. 1 and 2. In some instances, bone graft may be prepacked into hollow interior 24 prior to insertion. In other instances, and subsequent to the removal of the threaded inserter, bone graft may be introduced into hollow interior 24 through threaded hole 26. In other instances, bone graft may be both prepacked into hollow interior 24 with additional bone graft introduced through threaded hole 26 into hollow interior 24 after insertion. As a result of the construction of bellows shaped shell 20, radiographic images of bone graft contained within hollow interior 24 may be taken by fluoroscopy or other suitable imaging devices through wall 22 subsequent to surgery so as to monitor the progress of fusion to endplates 12a and 14a of vertebral bodies 12 and 14, respectively.

Having described the details of bellows shaped spinal implant 10 herein, it should be appreciated that when formed of titanium, bellows shaped spinal implant 10 may be used as interbody device that mimics the desirable properties of a similarly sized PEEK implant while maintaining the benefits of titanium, such as strength and osteointegration capability. In addition, low stiffness as provided by bellows shaped implant 10 assists in mimicking the biomechanical properties of the spine to help promote uniform endplate contact and load sharing with bone graft.

Figure 9:
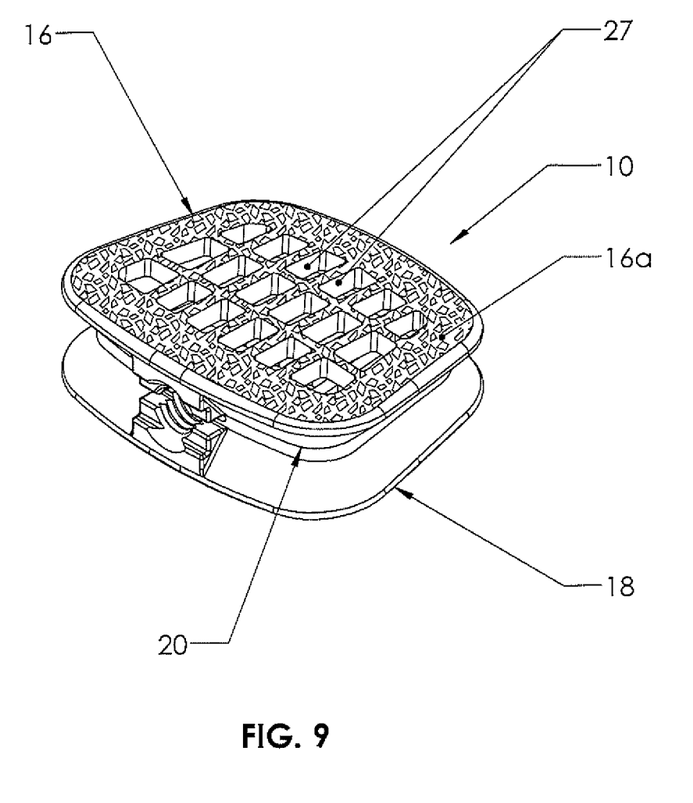
FIG. 9 is a top perspective view of a variation of the bellows shaped ALIF as seen from the anterior direction.
Figure 10:
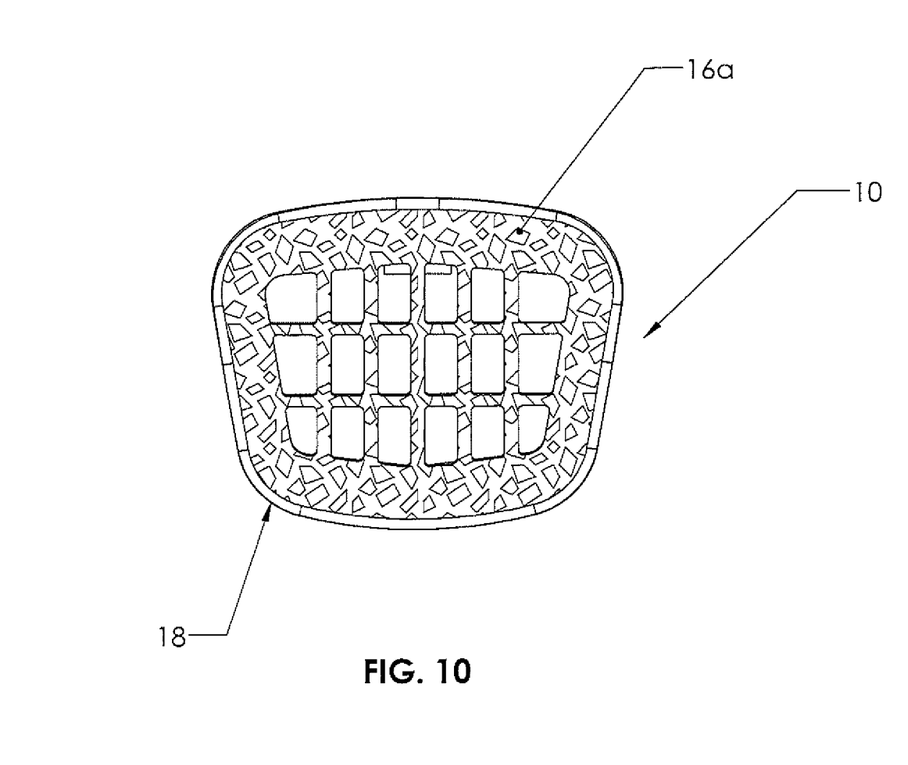
FIG. 10 is a top plan view of the bellows shaped ALIF device of FIG. 9.

While a preferred embodiment of bellows shaped spinal implant 10 as described herein is formed of pure titanium, it should also be appreciated that titanium alloys may also be used with similar beneficial results. Further, it should be understood that other variations may be made within the contemplated scope of the invention. For example, as shown in FIGS. 9 and 10, upper plate 16 and lower plate 18 of bellows shaped spinal implant 10 may be formed to have a plurality of fenestrations or smaller holes 27 instead of single central openings 16b and 18b. Such holes 27 will still permit fusion therethrough of interior bone graft material to vertebral body endplates 12a and 14a, while the increased surface area of contact surfaces 16a and 18a will allow increased implant strength and enhanced contact surface area to vertebral body endplates 12a and 14a.

Figure 11:
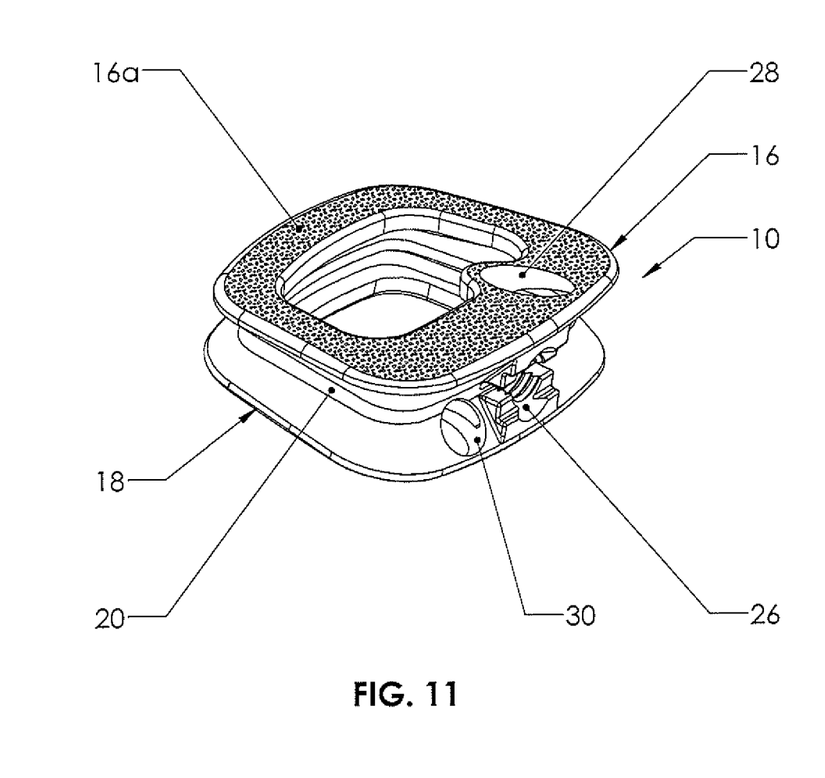
FIG. 11 is a top perspective view of further variation of the bellows shaped ALIF configured as a stand-alone device as seen from the anterior direction.
Figure 12:
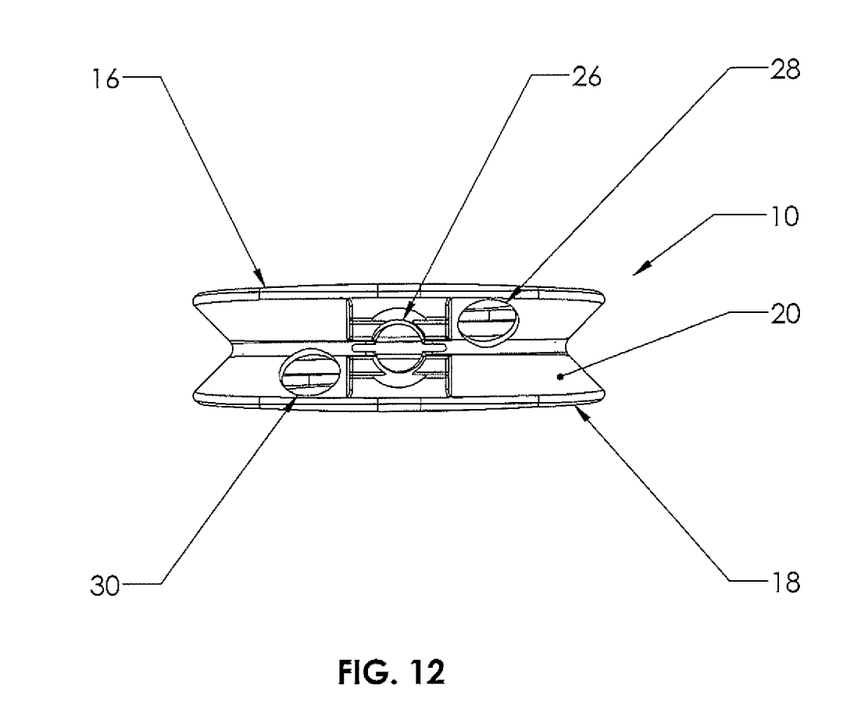
FIG. 12 is an anterior elevation view of the stand-alone bellows shaped ALIF device of FIG. 11.
Figure 13:
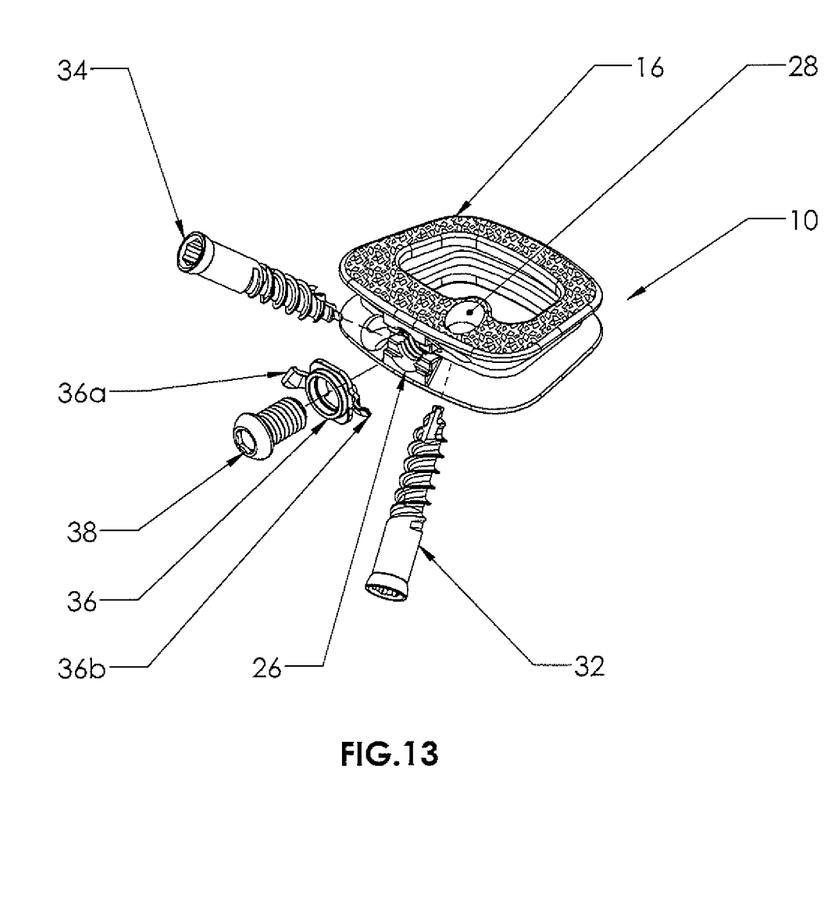
FIG. 13 is a top, anterior perspective view of the stand-alone bellows shaped ALIF device of FIG. 11 with exploded fixation screws and locking elements.

While bellows shaped spinal implant 10 has been described hereinabove as a conventional ALIF device for use with supplemental fixation, bellows shaped spinal implant 10 may also be configured as a stand-alone device. As shown in FIGS. 11 through 13, upper plate 16 and lower plate 18 may be formed to have fixation openings 28 and 30 angularly formed therethrough adjacent threaded hole 26 for receipt of fixation screws 32 and 34, respectively. Fixation screws 32 and 34 may be threadably attached to vertebral body endplates 14 and 12 through openings 28 and 30, respectively. A suitable locking element 36 comprising oppositely extending projections 36a and 36b may be provided to prevent fixation screws 32 and 34 from backing out subsequent to implant insertion. Locking element 36 may be attached to bellows shaped spinal implant 10 by a suitable locking screw 38 that is threaded into threaded opening 26 of spinal implant 10. Upon attachment of locking element 36 to spinal implant 10 by locking screw 38, projections 36a and 36b are configured to overlie fixation screws 32 and 34, respectively, in a manner to keep fixation screws 32 and 34 from backing out of vertebral bodies 12 and 14. Locking element 36 and locking screw 38 may be formed of PEEK material so as to minimize imaging artifacts and to maintain a desired stiffness of spinal implant 10.

While the invention has been illustrated and described in detail in the drawings and foregoing description, the same should be considered as illustrative and not restrictive in character. Accordingly, it is understood that only the preferred embodiments have been presented and that all changes, modifications and further applications that come within the spirit of the invention are desired to be protected.

What is claimed is:

1. A bellows shaped spinal implant, comprising:
    an upper plate having an outer upper contact surface and at least one upper opening therethrough;
    a lower plate having an outer lower contact surface and at least one lower opening therethrough; and
    a bellows shaped shell extending between and joining said upper plate and said lower plate, said bellows shaped shell being formed of titanium or an alloy comprising titanium and including a wall extending therearound that defines a hollow interior in communication with said at least one upper opening and said at least one lower opening, said wall having a thickness in the range of 0.5 mm to 1.0 mm, said wall being angled or curved between said upper plate and said lower plate, said wall including an insertion portion having a thickness greater than the thickness of the remainder of said wall, said insertion portion comprising a hole formed therethrough in communication with said hollow interior of said bellows shaped shell, and said hole configured for introducing bone graft into the hollow interior of said bellows shaped shell.

2. The bellows shaped implant of claim 1, wherein said outer upper contact surface and said outer lower contact surface each include a porous surface comprising a micro roughness.

3. The bellows shaped implant of claim 2, wherein said porous surface of each of said outer upper contact surface and said outer lower contact surface is 3-D printed defining a plurality of pores therethrough in communication with said hollow interior.

4. The bellows shaped implant of claim 3, wherein said porous surface of each of said outer upper contact surface and said outer lower contact surface further comprises a nano roughness.

5. The bellows shaped implant of claim 4, wherein said nano roughness is formed by laser ablation with a femto-second laser.

6. The bellows shaped implant of claim 4, wherein said nano roughness is formed by acid etching.

7. The bellows shaped implant of claim 1, wherein each of said upper plate and said lower plate has a thickness greater than the thickness of said wall.

8. The bellows shaped implant of claim 1, wherein said upper plate, said lower plate and said bellows shaped shell are formed unitarily as a one-piece bellows shaped spinal implant.

9. The bellows shaped implant of claim 1, wherein said wall further comprises a slit extending laterally into said insertion portion.

10. The bellows shaped implant of claim 9, wherein the hole through said insertion portion is threaded for attachment to a threaded inserter.

11. A bellows shaped spinal implant, comprising:
an upper plate having at least one upper opening therethrough;
a lower plate having at least one lower opening therethrough; and
a bellows shaped shell extending between and joining said upper plate and said lower plate, said bellows shaped shell being formed of titanium or an alloy comprising titanium and including a wall extending therearound that defines a hollow interior in communication with said at least one upper opening and said at least one lower opening, said wall having a thickness in the range of 0.5 mm to 1.0 mm, said wall being angled or curved between said upper plate and said lower plate,
said wall including an insertion portion having a thickness greater than the thickness of the remainder of said wall, said insertion portion comprising a threaded hole for attachment to a threaded inserter;
wherein said upper plate and said lower plate each have a fixation opening angularly formed therethrough for receipt of a fixation element, respectively, each fixation opening further extending through said wall of said bellows shaped shell.

12. The bellows shaped implant of claim 11, wherein each of said outer upper contact surface and said outer lower contact surface is planar.

13. The bellows shaped implant of claim 11, wherein said outer upper contact surface and said outer lower contact surface are formed at an angle relative to each other.

14. The bellows shaped implant of claim 11, wherein said at least one upper opening comprises a plurality of fenestrations and said at least one lower opening comprises a plurality of fenestrations.

15. The bellows shaped implant of claim 11, wherein said wall of said bellows shaped shell is angled or curved inwardly between said upper plate and said lower plate at an inclusive angle beta, $\beta$ in a range from a minimum of 0° to a maximum of 180°.

16. The bellows shaped implant of claim 14, wherein said thickness of the wall of said bellows shaped shell is 0.5 mm and the angle beta, $\beta$ of said bellows shaped wall is 90°.

17. The bellows shaped implant of claim 16, wherein said wall of said bellows shaped shell further comprises a slit extending laterally into said insertion portion.

18. A bellows shaped spinal implant, comprising:
an upper plate including an outer upper contact surface comprising a 3-D printed porous surface with a micro roughness defining a plurality of pores extending therethrough, and at least one upper opening formed therethrough;
a lower plate including an outer lower contact surface comprising a 3-D printed porous surface including a micro roughness defining a plurality of pores extending therethrough, and at least one lower opening formed therethrough; and
a bellows shaped shell extending between and joining said upper plate and said lower plate, said bellows shaped shell being formed of titanium or an alloy comprising titanium and including a wall extending therearound that defines a hollow interior in communication with said pores and said at least one upper opening of said upper plate and said pores and said at least one lower opening of said lower plate, said wall being angled or curved between said upper plate and said lower plate, said wall including an insertion portion with a thickness greater than a thickness of the remainder of said wall, said insertion portion comprising a threaded hole formed therethrough in communication with said hollow interior of said bellows shaped shell, said wall having a slit extending laterally into said insertion portion, and said threaded hole configured for introducing bone graft into the hollow interior of said bellows shaped shell or for attachment to a threaded inserter.

19. The bellows shaped implant of claim 18, wherein said porous surface of each of said outer upper contact surface and said outer lower contact surface further comprises a nano roughness.

20. The bellows shaped implant of claim 19, wherein said nano roughness of each of said outer upper contact surface and said outer lower contact surface is formed by laser ablation with a femto-second laser.

21. The bellows shaped implant of claim 19, wherein said nano roughness of each of said outer upper contact surface and said outer lower contact surface is formed by acid etching.

22. The bellows shaped implant of claim 18, wherein said wall of said bellows shaped shell is angled or curved inwardly between said upper plate and said lower plate at an inclusive angle beta, $\beta$.

23. A bellows shaped spinal implant, comprising:

an upper plate having an outer upper contact surface and at least one upper opening therethrough;

a lower plate having an outer lower contact surface and at least one lower opening therethrough; and a bellows shaped shell extending between and joining said upper plate and said lower plate, said bellows shaped shell being formed of titanium or an alloy comprising titanium and including a wall extending continuously therearound that defines a hollow interior in communication with said at least one upper opening and said at least one lower opening, said wall being angled or curved between said upper plate and said lower plate, said wall having a thickness in the range of 0.5 mm to 1.0 mm that is configured and dimensioned to achieve radiographic imaging through said wall, said wall being configured and dimensioned to provide stiffness that mimics stiffness properties of a similarly sized polyetheretherketone (PEEK) implant, said wall including an anterior portion having a thickness greater than the thickness of the remainder of said wall, said anterior portion comprising an attachment feature for attachment to an inserter, and said wall comprising at least one opening angularly formed therethrough in communication with said hollow interior of said bellows shaped shell, said at least one opening configured for receipt of a fixation element.

24. The bellows shaped implant of claim 23, wherein said at least one opening further extends through one of said upper plate or said lower plate.

25. The bellows shaped implant of claim 23, wherein said wall of said bellows shaped shell is angled or curved between said upper plate and said lower plate at an angle to provide stiffness that mimics stiffness properties of a similarly sized polyetheretherketone (PEEK) implant.

26. The bellows shaped implant of claim 23, wherein said upper plate, said lower plate and said bellows shaped shell comprise a 3-D printed one-piece bellows shaped spinal implant.

27. The bellows shaped implant of claim 23, wherein said outer upper contact surface comprises a porous surface defining a plurality of pores extending therethrough in communication with said hollow interior of said bellows shaped shell, and wherein said outer lower contact surface comprises a porous surface defining a plurality of pores extending therethrough in communication with said hollow interior of said bellows shaped shell.

28. The bellows shaped implant of claim 27, wherein said porous surface of said outer upper contact surface further comprises a nano roughness, and wherein said porous surface of said outer lower contact surface further comprises a nano roughness.

29. The bellows shaped implant of claim 23, wherein said attachment feature includes a threaded hole for attachment to a threaded inserter.

* * * * *